(12) United States Patent
Tsim et al.

(10) Patent No.: US 6,569,625 B1
(45) Date of Patent: May 27, 2003

(54) FRITILLARIA SPECIES IDENTIFICATION

(75) Inventors: Karl W. K. Tsim, Stanley (HK); Nancy Y. Ip, Hong Kong (HK); Nikolaus J. Sucher, Clear Water Bay (HK)

(73) Assignee: The Hong Kong University of Science & Technology, Kowloon (HK)

( * ) Notice: Subject to any disclaimer, the term of this patent is extended or adjusted under 35 U.S.C. 154(b) by 0 days.

(21) Appl. No.: 09/709,840

(22) Filed: Nov. 10, 2000

Related U.S. Application Data

(63) Continuation of application No. 09/352,061, filed on Jul. 14, 1999, now abandoned.

(51) Int. Cl.$^7$ .............................. C12Q 1/68; C12Q 1/48; C12Q 1/44; C12P 19/34; C07H 21/04
(52) U.S. Cl. ..................... 435/6; 435/15; 435/19; 435/91.2; 435/810; 536/23.1; 536/23.6; 536/24.3; 536/24.33
(58) Field of Search ................. 435/6, 15, 19, 435/91.2, 810; 536/23.1, 23.6, 24.3, 24.33

(56) References Cited

U.S. PATENT DOCUMENTS

| | | | |
|---|---|---|---|
| 5,723,507 A | 3/1998 | Markovich et al. | 521/51 |
| 5,738,988 A | 4/1998 | Kohne | 435/6 |
| 5,849,492 A | 12/1998 | Rogan | 435/6 |

FOREIGN PATENT DOCUMENTS

| | | |
|---|---|---|
| WO | WO 93/23568 | 11/1993 |

OTHER PUBLICATIONS

Cai, Z.H. et al, "Molecular Diversity of 5S—rRNA Spacker Domain in *Fritillaria* Species Revealed by PCR Analysis", Planta Medica 65 (1999) New York, pp. 360–364.
Gao, W. et al, "Preliminary analysis of isolation of genomic total DNA in *Fritillaria thunbergii* Mig.", Zhongguo Zhongyao Zazhi 23(2):79–81, Abstract only.
Udovicic, F. GenEmbl Accession No. AF049455.
Udovicic, F. Gen Embl Accession No. AF049419.
Udovicic, F. GenEmbl Accession No. AF049447.
Udovicic, F. Gen Embl Accession No. AF049428.
Erlich, H.A. et al, "Recent Advances in the Polymerase chain Reaction", Science 252: 1643–51.
Johnson, D.A. et al, Structure of the 5S rRNA genes in birth (*Betula papyrifera*) and alder (*Alnus incana*) Genome 35 (2) 337–341.
Brandham, P.E. et al, "Genome Size in the Aloaceae, an Angiosperm Family Displaying Karyotypic Orthoselection", Annals of Botany 82 (Suppl A): 67–73.

*Primary Examiner*—Carla J. Myers
*Assistant Examiner*—Diana Johannsen
(74) *Attorney, Agent, or Firm*—Dority & Manning, PA

(57) ABSTRACT

According to the present invention there is provided a method for determining the phylogeny of sample Fritillaria genetic material.

13 Claims, 9 Drawing Sheets

Figure 3A

```
F.cirrhosa    GGATCCGTGCTTGGGCGAGAGTAGTACTAGGATGGGTGACCTCCTGGGAAGTCCTCGT-G
F.anhuiensis  GGATCCGTGCTTGGGCGAGAGTAGTACTAGGATGGGTGACCTCCTGGGAAGTCCTCGTTG
F.puqiensis   GGATCCGTGCTTGGGCGAGAGTAGTACTAGGATGGGTGACCTCCTGGGAAGTCCTCGTTG
F.thunbergii  GGATCCGTGCTTGGGCGAGAGTAGTACTAGGATGGGTGACCTCCTGGGAAGTCCTCGTTG
              ******************************************************** *
                           S-1

F.cirrhosa    TTGCACCCCCAACCCCCTCTTTTGTCGCATCATTTTGTCGCATCATGAGAAATGCGCACG
F.anhuiensis  TTGCACCCCCTCCCCCCT--------------TTTTGTCGCATCCTGAGAAATAAGCACG
F.puqiensis   TTGCACCCCCTCCCCCCT--------------TTTTGTCGCATCCTGAGAAATACGCACG
F.thunbergii  TTGCACCCCCTCCCCCCT--------------TTTTGTCGCATCCTGAGAAATACGCACG
              ********** ******              ************ ******* ****

F.cirrhosa    TCCACCTTTTGTGCGCCTCGCCCTAAATAGGCGGGCGAGGTAACATCGTGTCGGCCTTTC
F.anhuiensis  TCCTCCTTTCGCGCGCCTCGCCCTAAATAGGCGGGCGAGCTAACATT-TGTCGGCCTTTC
F.puqiensis   TCCTCCTTTTGCGCGCCTCGCCCTAAATAGGCGGGCGAGCTAACATT-TGTCGGCCTTTC
F.thunbergii  TCCTCCTTTTGCGCGCCTCGCCCTAAATAGGCGGGCGAGCTAA-------TCGGCCTTTC
              *** ***** * ************************** ***        *********

F.cirrhosa    ATTTTACGGGTTTTGGCGG----------------GCCCGCTTT-CGATAC--GGGGGGC
F.anhuiensis  ATTTGCGGGTTTTGGCGGCACAAAACGGGGCGGGCCCGCTTTTCGATAACGGGGGGGC
F.puqiensis   ATTTGCGGGTTTTGGCGGCACAAAACGGGGCGGGCCCGCTTTTCGATAACGGGGGGGC
F.thunbergii  ATTTGCGGGTTTTGGCGGCACAAAACGGGGCGGGCCCGCTTTTCGATAACGGGGGGGC
              **** *************                ********* ****   *******

F.cirrhosa    GAGCTGGCTATTTTCTCGATGGTTTGATAAGAATAAGTCAAAATATGAGTTTGTGAATTC
F.anhuiensis  GAAGTGGCTATTTTCTCGATGGTTTGATGAGAATAAGTCAAAATTTGAGTTTGCGAATAC
F.puqiensis   GAAGTGGCTATTTTCCCGATGGTTTGATGAGAATAAGTCAAAATTTGAGTTTGTGAATAC
F.thunbergii  GAAGTGGCTATTTTCCCGATGGTTTGATGAGAATAAGTCAAAATTTGAGTTTGTGAATAC
              ** ************ *********** ************ **** ******* **** *

F.cirrhosa    TAATAATTGGTTAATTAGCTTTCACCTTATGCTCGGTGAGAT-AGATCGTAATTTCGGTT
F.anhuiensis  TAAT-----------TAACTTTCGCTCTATGCTTGGTGAGATTAGATCATAATTTCGGTT
F.puqiensis   TAAT-----------TAACTTTCGCTTTATGCTTGGTGAGATTAGATCATAATTTCGGTT
F.thunbergii  TAAT-----------TAACTTTCGCTTTATGCTTGGTGAGATTAGATCATAATTTCGGTG
              ****           ** ***** * ****** ******** ***** **********

F.cirrhosa    TATAAATATTAATATTTTGTTAATTATTTTACTTTACTTTAAGATAAATAAGATTAATTC
F.anhuiensis  TATTAATATTGATATTTTGTCAATTAACTTT-TTTACTATAAGATAAATAAGATTAATTC
F.puqiensis   TATTAATATTGATATTTTGTCAATTAACTTT-TTTACTATGAGATAAATAGGATTAATTC
F.thunbergii  TATTAATATTGATATTTTGTCAATTAACTTT-TTTACTATGAGATAAATAGGATTAATTC
              *** ****** ********* **  ****** * ****** * ******** ********

F.cirrhosa    CTAAGTCCGGTTTAATAACGGTAATATATCG-CAAATTAACTTTTACTCCGCGTCTAATG
F.anhuiensis  CAAAGTTCGGCTTATTAACGGTAATATATCGTCAAATTAACTTTGCTCCGTGTTTAATG
F.puqiensis   CAAAGTTCGGTTTATTAATGGTAATATATCG-CAAATTAACTTTTACTGCGTGTTTAGTG
F.thunbergii  CAAAGTTCGGTTTATTAATGGTAATATATCG-CAAATTAACTTTTACTGCGTGTTTAGTG
              * **** *** *** *** ************ ************ ** ** ** ** **

F.cirrhosa    AGAAAAGGTAATAATATATGTTTATTGATACTAATACGTAATGTTAGCGGGCATTTACTT
F.anhuiensis  AGAATAAGTCGTAATATTCGTTTATTGATACTAATACGTAATGTTAGCGGGAATTTACTG
F.puqiensis   AGAATAAGTCGTAATATTCGTTTATTGATACTAATACGTAATGTTAGCGGGAATTTACTG
F.thunbergii  AGAATAAGTCGTAATATTCGTTTATTGATACTAATACGTAATGTTAGCGGGAATTTACAT
              **** * ** ****** ********************************* ******
```

Figure 3B

```
F.cirrhosa      TGTGTGCTAATCCATAAATTCGACCGATTAATGCTAATATTTTAATAATTGGCTCTCGCT
F.anhuiensis    TGTGTACTAATCCACAAATTCGATCGATTAATGCAAATACTTCAATAATTGGCTCTCGCT
F.puqiensis     TGTGTACTAATCCACAAATTCGATCGATTAATGCTAATACTTTAATAATTGGCTCTCGCT
F.thunbergii    TGTGTACTAATCCATGAATTCGATCGATTAATGCTAATACTTTAATAATTGGCTCTCGCT
                ****  ********  ****** **********  ****  ** *******************

F.cirrhosa      TTCCGTTTAGTA-GGATTAACTCCTAGTTTTGAAGCCCGTGGAAGAGGAATAAGAGGAAG
F.anhuiensis    TTCCGTGTAATA-GGATTAACTCCTAATTTTGAATCCCGTGGAAGAGGAATAAGTGGAAG
F.puqiensis     TTCCGTGTAATAAGGATTAACTCCTAATTTTGAATCCCGTGGAAGAGGAATAAGTGGAAG
F.thunbergii    TTCCGTGTAATAAGGATTAACTCCTAATTTTGAATCCCGTGGAAGAGGAATAAGTGGAAG
                ******ss** ** ************* ****** ******************** *****

F.cirrhosa      GGGAAGGAAACATATGACGGGTGCGATCATACCAGCACTAAGGATCC
F.anhuiensis    GGGAAGGAAACATATGACGGGTGCGATCATACCAGCACTAAGGATCC
F.puqiensis     GGGAAGGAAACATATGACGGGTGCGATCATACCAGCACTAAGGATCC
F.thunbergii    GGGAAGGAAACATATGACGGGTGCGATCATACCAGCACTAAGGATCC
                ***********************************************
                                  ―――――――――――――――――――――――――――――――
                                                 AS-1
```

Figure 5A

```
F.cir.var.vir    GGATCCGTGCTTGGGCGAGAGTAGTACTAGGATGGGTGACCTCCTGGGAAGTCCTCGT-G
F.tortifoliae    GGATCCGTGCTTGGGCGAGAGTAGTACTAGGATGGGTGACCTCCTGGGAAGTCCTCGT-G
F.unbracteata    GGATCCGTGCTTGGGCGAGAGTAGTACTAGGATGGGTGACCTCCTGGGAAGTCCTCGC-G
F.pallidifl      GGATCCGTGCTTGGGCGAGAGTAGTACTAGGATGGGTGACCTCCTGGGAAGTCCTCGTTG
F.hubeinesis     GGATCCGTGCTTGGGCGAGAGTAGTACTAGGATGGGTGACCTCCTGGGAAGTCCTCGT-G
F.cir.var.pur    GGATCCGTGCTTGGGCGAGAGTAGTACTAGGATGGGTGACCTCCTGGGAAGTCCTCGT-G
F.puqiensis      GGATCCGTGCTTGGGCGAGAGTAGTACTAGGATGGGTGACCTCCTGGGAAGTCCTCGTTG
F.delavayi       GGATCCGTGCTTGGGCGAGAGTAGTACTAGGATGGGTGACCTCCTGGGAAGTCCTCGT-G
F.thunbergii     GGATCCGTGCTTGGGCGAGAGTAGTACTAGGATGGGTGACCTCCTGGGAAGTCCTCGTTG
F.taibainesis    GGATCCGTGCTTGGGCGAGAGTAGTACTAGGATGGGTGACCTCCTGGGAAGTCCTCGT-G
F.anhuiensis     GGATCCGTGCTTGGGCGAGAGTAGTACTAGGATGGGTGACCTCCTGGGAAGTCCTCGTTG
F.ussunensis     GGATCCGTGCTTGGGCGAGAGTAGTACTAGGATGGGTGACCTCCTGGGAAGTCCTCGT-G
F.tianmuensis    GGATCCGTGCTTGGGCGAGAGTAGTACTAGGATGGGTGACCTCCTGGGAAGTCCTCGTTG
F.prezwalskii    GGATCCGTGCTTGGGCGAGAGTAGTACTAGGATGGGTGACCTCCTGGGAAGTCCTCTT-G
F.cir            GGATCCGTGCTTGGGCGAGAGTAGTACTAGGATGGGTGACCTCCTGGGAAGTCCTCGT-G
F.cirrhosa       GGATCCGTGCTTGGGCGAGAGTAGTACTAGGATGGGTGACCTCCTGGGAAGTCCTCGT-G
                 ************************************************ *     *

F.cir.var.vir    TTGCACCCCCAA-CCCCCTCTTTTGTCGCATCATT-------------TTGTCGCATCAT
F.tortifoliae    TTACACCCCCTC-CCCCCT--------------TT-------------TTGTCGCATCCT
F.unbracteata    TTGCACCCCCAA-CCCCCTC-------------TT-------------TTGTCGCATCAT
F.pallidifl      TTACACCCCCTC-CCCCCT--------------TT-------------TTGTCGCATCCT
F.hubeinesis     TTGCACCCCCTA-CCCCCTCTTTTGTCGCATCATTGTGTCGCATCATCTTGTCGCATCAT
F.cir.var.pur    TTGCACCCCCAA-CCCCCTCTTTTGTCGCATCATT-------------TTGTCGCATCAT
F.puqiensis      TTGCACCCCCTC-CCCCCT--------------TT-------------TTGTCGCATCCT
F.delavayi       TTGCACCCCCTA-CCCCCTCTTTTGTCGCATCATTGTGTCGCATCATCTTGTCGCATCAT
F.thunbergii     TTGCACCCCCTC-CCCCCTTTTT------------------------GTCGCATCCT
F.taibainesis    TTGCACCCCCTA-CCCCCTCTTTTGTCGCATCATTGTGTCGCATCATCTTGTCGCATCAT
F.anhuiensis     TTGCACCCCCTC-CCCCCTTTTT------------------------GTCGCATCCT
F.ussunensis     TTGCACCCCCTA-CCCCCTCTTTTGTCGCATCATTGTGTCGCATCATCTTGTCGCATCAT
F.tianmuensis    TTGCACCCCCTC-CCCCCTTTTT------------------------GTCGCATCCT
F.prezwalskii    TTACACCCCCT--CCCCCCTTTTTGTG---------------------ATCCT
F.cir            TTGCACCCCCCAACCCCCTCTTTTGTCGCATCAT--T-----------TTATCGCATCAT
F.cirrhosa       TTGCACCCCCAA-CCCCCTCTTTTGTCGCATCATT-------------TTGTCGCATCAT
                 ** *******    *****                                *** *

F.cir.var.vir    GAGAAATGCGCACGT-CCTCCTTTTGTGCG-CCTCGCCCTAAATAGGCGGGCGAGGTAAC
F.tortifoliae    GAGAAATACGCACGT-CCTCCTTTTGCGTT-CCTCGCCCTAAATAGGCGGGCGAGCTAAC
F.unbracteata    GAGAAATGCGCACGT-CCTCCTTTTGCG-CCTCGCC-TAAATAGGCGGGCGAGGTAAC
F.pallidifl      GAGAAATACGCACGT-CCTCCTTTTGCGTT-CCTCGCCCTAAATAGGCGGGCGAGCTAAC
F.hubeinesis     GAGAAATGCGCACGT-CCTCCTTTTGTGCG-CCTCGCCCTAAATAGGCGGGCGAGGTAAC
F.cir.var.pur    GAGAAATGCGCACGT-CCACCTTTTGTGCG-CCTCGCCCTAAATAGGCGGGCGAGGTAAC
F.puqiensis      GAGAAATACGCACGT-CCTCCTTTTGCGCG-CCTCGCCCTAAATAGGCGGGCGAGCTAAC
F.delavayi       GAGAAATGCGCACGT-CCTCCTTTTGTGCG-CCTCGCCCTAAATAGGCGGGCGAGGTAAC
F.thunbergii     GAGAAATACGCACGT-CCTCCTTTTGCGCG-CCTCGCCCTAAATAGGCGGGCGAGCTAA-
F.taibainesis    GAGAAATGCGCACGT-CCTCCTTTTGTGCG-CCTCGCCCTAAATAGGCGGGCGAGGTAAC
F.anhuiensis     GAGAAATAAGCACGT-CCTCCTTTCGCGCG-CCTCGCCCTAAATAGGCGGGCGAGCTAAC
F.ussunensis     GAGAAATGCGCACGT-CCTCCTTTTGTGCG-CCTCGCCCTAAATAGGCGGGCGAGGTAAC
F.tianmuensis    GAGAAATACGCACGT-CCTCCTTTTGTGCG-CCTCGCCCTAAATAGGCGGGCGAGCTAAC
F.prezwalskii    GAGAAATACGCACGTTCCTCCTTTTGCCTTTCCTCGCCCTAAATAGGCGGGCGAGCTAAC
F.cir            GAGAAATGCGCACGT-CCTCCTTTTGTGCG-CCTCGCCCTAAATAGGCGGGCGAGGTAAC
F.cirrhosa       GAGAAATGCGCACGT-CCTCCTTTTGTGCG-CCTCGCCCTAAATAGGCGGGCGAGGTAAC
                 ******* ****** ** ***** *  ****** **************** ***
```

Figure 5B

```
F.cir.var.vir    ATCGTGTCGGCCTTTCATTTTACGGGTTTTGGCGG----------------GCCCGCTT
F.tortifoliae    ATTTTGTCGCCCTTTCATTTTGCGGGTTTTGGCGGCACAAAA-CGGGGGCGGGCCTCTTT
F.unbracteata    ATCGTGTCGGCCTTTCATTTTACGGGTTTTGGCGGGCCC---------GCC-------TT
F.pallidifl      ATTTTGTCGCCCTTTC-TTTTGCGGGTTTTGGCCGGCACAAAACGGGGGCCGGGCCTCTT
F.hubeinesis     ATCGTGTCGGCCTTTCATTTTACGGGTTTTGGCGG----------------GCCCGCTT
F.cir.var.pur    ATCGTGTCGGCCTTTCATTTTACGGGTTTTGGCGG----------------GCCCGCTT
F.puqiensis      ATT-TGTCGGCCCTTTCATTTTGCGGGTTTTGGCGGCACAAAA-CGGGGGCGGGCCCGCTT
F.delavayi       ATCGTGTCGGCCTTTCATTTTACGGGTTTTGGCGG----------------GCCCGCTT
F.thunbergii     ------TCGGCCTTTCATTTTGCGGGTTTTGGCGGCACAAAA-CGGGGGCGGGCCCGCTT
F.taibainesis    ATCGTGTCGGCCTTTCATTTTACGGGTTTT-----------------GGCGGGCCCGCTT
F.anhuiensis     ATT-TGTCGGCCTTTCATTTTGCGGGTTTTGGCGGCACAAAA-CGGGGGCGGGCCCGCTT
F.ussunensis     ATCGTGTCGGCCTTTCATTTTACGGGTTTTGGCGG----------------GCCCGCTT
F.tianmuensis    ATTTTGTCGGCCTTTCATTTTGCGGGTTTTGGCGGCACAAAA-CGGGGGCGGGCCCGCTT
F.prezwalskii    ATTTTGTCGCCCTTTCATTTTGCGGGTTTTGGCGGCACAAAA-CGGGGGCGGGCCCTCTT
F.cir            ATCGTGTCGGCCTTTCATTTTACGGGTTTTGGCGG-----------G------CCCGCTT
F.cirrhosa       ATCGTGTCGGCCTTTCATTTTACGGGTTTTGGCGG----------------GCCCGACT
                 *** ****** **** ********                              *

F.cir.var.vir    T-CGATAC---GGGGGGC----GAGCTGGCTATTTTCTCGATGGTTTGATAAGAATAAGT
F.tortifoliae    T-CGATAACG-GGGGGGC----GAAGTGGCTATTTTCCCGATGGTTTGATGAGAATAAGT
F.unbracteata    T-CGATA--C-GGGGGGC----GAGCTGGCTATTTTCTCGATGGTTTGATAAGAATAAGT
F.pallidifl      T-TGATAA-C-GGGGGGCTCGGGAAGTGGCTATTTTCCCGATGGTTTGATGAGAATAAGT
F.hubeinesis     T-CGATAC---GGGGGGC----GAGCTGGCTATTTTCTCGATGGTTTGATAAGAATAAGT
F.cir.var.pur    T-CGATAC---GGGGGGC----GAGCTGGCTATTTTCTCGATGGTTTGATAAGAATAAGT
F.puqiensis      TTCGATAACG-GGGGGGC----GAAGTGGCTATTTTCCCGATGGTTTGATGAGAATAAGT
F.delavayi       T-CGATAC---GGGGGGC----GAGCTGGCTATTTTCTCGATGGTTTGATAAGAATAAGT
F.thunbergii     TTCGATAACG-GGGGGGC----GAAGTGGCTATTTTCCCGATGGTTTGATGAGAATAAGT
F.taibainesis    T-CGATAC---GGGGGGC----GAGCTGGCTATTTTCTCGATGGTTTGATAAGAATAAGT
F.anhuiensis     TTCGATAACG-GGGGGGC----GAAGTGGCTATTTTCCCGATGGTTTGATGAGAATAAGT
F.ussunensis     T-CGATAC---GGGGGGC----GAGCTGGCTATTTTCTCGATGGTTTGATAAGAATAAGT
F.tianmuensis    TTCGATAACGGGGGGGGC----GAAGTGGCTATTTTCCCGATGGTTTGATGAGAATAAGA
F.prezwalskii    TTCGATAAC--GGGGGGT----GAAGTGGCTATTTTC-CGATGGTTTGATGAGAATAAGT
F.cir            T-CGATA----CGGGGGA----GAGCTGGCTATTTTCTCGATGGTTTGATAAGAATAAGT
F.cirrhosa       TTCGATAC---GGGGGGC----GAGCTGGCTATTTTCTCGATGGTTTGATAAGAATAAGT
                 * ****      *****     **  ********** ************* *******

F.cir.var.vir    -CAAAATATGAGTTTGTGAATTCTAATAATTGGTTAATTAGCTTTCACCTT-AT-GCTCG
F.tortifoliae    -CAAAATTTGAGTTTCTGAATACTAAT-----------TAACTTTCGCTTT-AT-GCTTG
F.unbracteata    -CAAAATATGAGTTTGTGAATTCTAATAATTGGTTAATTAGCTTTCACCTT-AT-GCTCG
F.pallidifl      -CAAAATTTGAGTTTGT-------AATAC-----TAATTAACTTTCTCGTTTATCGTTTG
F.hubeinesis     -CAAAATATAAGTTTGTGAATTCTAATAATTGGTTAATTAGCCTTCACCTT-AT-GCTCG
F.cir.var.pur    -CAAAATATGAGTTTGTGAATTCTAATAATTGGTTAATTAGCTTTCACCTT-AT-GCTCG
F.puqiensis      -CAAAATTTGAGTTTGTGAATACTAAT-----------TAACTTTCGCTTT-AT-GCTTG
F.delavayi       -CAAAATATAAGTTTGTGAATTCTAATAATTGGTTAATTAGCCTTCACCTT-AT-GCTCG
F.thunbergii     -CAAAATTTGAGTTTGTGAATACTAAT-----------TAACTTTCGCTTT-AT-GCTTG
F.taibainesis    -CAAAATATAAGTTTGTGAATTCTAATAATTGGTTAATTAGCCTTCACCTT-AT-GCTCG
F.anhuiensis     -CAAAATTTGAGTTTGCGAATACTAAT-----------TAACTTTCGCTCT-AT-GCTTG
F.ussunensis     -CAAAATATAAGTTTGTGAATTCTAATAATTGGTTAATTAGCCTTCACCTT-AT-GCTCG
F.tianmuensis    -CTTTTTTTGAGTTTGTGAATACTAAT-----------TAACTTTCGCTTT-AT-GCTTG
F.prezwalskii    TCAAAATTTGAGTTTCTGAATACTAAT-----------TTAACTTTCGCTTT-AT-GCTTG
F.cir            -CAAAATATGAGTTTGTGAATTCTAATAATTGGTTAATTAGCTTTCACCTT-AT-GCTCG
F.cirrhosa       -CAAAATATGAGTTTGTGAATTCTAATAATTGGTTAATTAGCTTTCACCTTATCCGATCG
                 *   * * *****     ***           ** * *** *    * * *
```

Figure 5C

```
F.cir.var.vir   GTGAGAT-AGATCGTAATTTCG-GTTTATAAATATTAATATTTTGTTAATTATTTTTTTT
F.tortifoliae   GTGAGATTAGATCATAATTTCG-GTTTGTTAATATCGATATTAGGTCAATTAACTTTTTT
F.unbracteata   GTGAGATAAGATCGTAATTTCG-GTTTATAAATATTAATATTTTGTTAATTATTTTTTTT
F.pallidifl     GTGAGATTAGATCATAATTTCG-GTTTGTTAATCATGATATTAGGCTAATTAACTTTTTT
F.hubeinesis    GTGAGATAAGATCGTAATTTCG-GTTCATAAATATTAATATTTTGTTAATTATTTTTTTT
F.cir.var.pur   GTGAGAT-AGATCGTAATTTCG-GTTTATAAATATTAATATTTTGTTAATTATTTTACTT
F.puqiensis     GTGAGATTAGATCATAATTTCG-GTTTATTAATATTGATATTTTGTCAATTAACTTT-TT
F.delavayi      GTGAGATAAGATCGTAATTTCG-GTTCATAAATATTAATATTTTGTTAATTATTTTT-TT
F.thunbergii    GTGAGATTAGATCATAATTTCG-GTGTATTAATATTGATATTTTGTCAATTAACTTT-TT
F.taibainesis   GTGAGATAAGATCGTAATTTCG-GTTCATAAATATTAATATTTTGTTAATTATTTTT-TT
F.anhuiensis    GTGAGATTAGATCATAATTTCG-GTTTATTAATATTGATATTTTGTCAATTAACTTT-TT
F.ussunensis    GTGAGATAAGATCGTAATTTCG-GTTCATAAATATTAATATTTTGTTAATTATTTTT-TT
F.tianmuensis   GTGAGATTAGATCATAATT-CG-GTG-ATTAATATTGATATTT-GTCCCTTAACTTT-TT
F.prezwalskii   GTGAGATTAGATCATAATTTTCAGTTTGTTAATATCGATATTAGGTCAATTAACTTT-TT
F.cir           GTGAGATAAGATCGTAATTTC--GGTTATAAATATTAATATTTG-TTAATTA--TTT-TT
F.cirrhosa      GTGAGATAAGATCGTAATTTCG-GTTTATAAATATTAATATTTTGTTAATTATTTTT-TT
                *******  ***** *****   *   * ***     *****    ***   **   **

F.cir.var.vir   TACTTTAAGATAAATAAGATTAATTCCTAAGTCCGGTTTAATAAC-GGTAA-TATATCG-
F.tortifoliae   -ACTATAAGATAAATAAGATTAATTCCAAAGTTCGGTTTATTAAT-GGTAA-TGTATCG-
F.unbracteata   TACTTTAAGATAAATAAGATTAATTCCTAAGTCCGGTTTAATAAC-GGTAA-TATATCG-
F.pallidifl     -ACTATAAGATAAATAAGATTAATTCCAAAGTTCGGTTTATTAAT-GGTAA-TGTATCG-
F.hubeinesis    -ACTTTAAGATAAATAAGATTAATTCCTAAGTCCGGTTTAATAAC-GGTAA-TATATCG-
F.cir.var.pur   TACTTTAAGATAAATAAGATTAATTCCTAAGTCCGGTTTAATAAC-GGTAA-TATATCG-
F.puqiensis     TACTATGAGATAAATAGGATTAATTCCAAAGTTCGGTTTATTAAT-GGTAA-TATATCG-
F.delavayi      TACTTTAAGATAAATAAGATTAATTCCTAAGTCCGGTTTAATAAC-GGTAA-TATATCG-
F.thunbergii    TACTATGAGATAAATAGGATTAATTCCAAAGTTCGGTTTATTAAT-GGTAA-TATATCG-
F.taibainesis   TACTTTAAGATAAATAAGATTAATTCCTAAGTCCGGTTTAATAAC-GGTAA-TATATCG-
F.anhuiensis    TACTATAAGATAAATAAGATTAATTCCAAAGTTCGGCTTATTAAC-GGTAA-TATATCGT
F.ussunensis    TACTTTAAGATAAATAAGATTAATTCCTAAGTCCGGTTTAATAAC-GGTAA-TATATCG-
F.tianmuensis   TACTATAAGATAAATAAGATTAATTCCAAAGTTCGGTTTATTAAT-GGTAA-TATATCG-
F.prezwalskii   TACTATAAGATAAATAAGATTAATTCCAAAGTTCGGTTTATTAAATGGTAAATGTATCG-
F.cir           TACTTTAAGATAAATAAGATTAATTCCAAAGTCCGGTTTAATAAC-GGTAA-TATATCG-
F.cirrhosa      TACTTTAAGATAAATAAGATTAATTCCTAAGTCCGGTTTAATAAC-GGTAA-TATATCG-
                *** * ********* ********** **** *** *** ***   ***** * *****

F.cir.var.vir   CAAATTAACTTTTACTCCGTGTCTAATGAGAAAA-GGTAATAATATATGTTTATTGATAC
F.tortifoliae   CAAATTAACTTTTACTCCGTGTTTAATGAGAATA-AGTCGTAATATTCGTTTATTGATAC
F.unbracteata   CAAATTAACTTTTACTCCGTGTCTAATGAGAAAA-GGTAATAATATATGTTAATTGATAC
F.pallidifl     CAAATTAACTTTTACTCCGTGTTTAATGAGAATA-AGTCGTAATATTCGTTTATTGATAC
F.hubeinesis    CAAATTAACTTTTACTCTGTGTCTAATGAGAAAA-GGTAATAATATATGCTTATTGATAC
F.cir.var.pur   CAAATTAACTTTTACTCCGCGTCTAATGAGAAAA-GGTAATAATATATGTTTATTGATAC
F.puqiensis     CAAATTAACTTTTACTCCGTGTTTAGTGAGAATA-AGTCGTAATATTCGTTTATTGATAC
F.delavayi      CAAATTAACTTTTACTCTGTGTCTAATGAGAAAA-GGTAATAATATATGCTTATTGATAC
F.thunbergii    CAAATTAACTTTTACTGCGTGTTTAGTGAGAATA-AGTCGTAATATTCGTTTATTGATAC
F.taibainesis   CAAATTAACTTTTACTCTGTGTCTAATGAGAAAA-GGTAATAATATATGCTTATTGATAC
F.anhuiensis    CAAATTAACTTTTGCTCCGTGTTTAATGAGAATA-AGTCGTAATATTCGTTTATTGATAC
F.ussunensis    CAAATTAACTTTTACTCTGTGTCTAATGAGAAAA-GGTAATAATATATGCTTATTGATAC
F.tianmuensis   CAAATTAACTTTTACAGCGTGTTTGGTGAGAATA-AGTCGTAATATTCGTTTATTGATAC
F.prezwalskii   CAAATTAACTTTTACTCCGTGTTTAATGAGAATA-AGTCGTAATATTCGTTTATTGATAC
F.cir           CAAATTAACTTTTACTCCGTGTTTAATGAGAAAA-GGTAATAATATATGTTTATTGATAC
F.cirrhosa      CAAATTAACTTTTACTCTGTGTCTAATGAGAAAAGGTAATAATATATGCTTATTGATAC
                ************ *   ** * ****** *  ** ****** * * ********
```

Figure 5D

```
F.cir.var.vir    -TAATACGTAATGTTAGCGGGCATTTACTTTGTGTGCTAATCCATAAATTCGACC-GATT
F.tortifoliae    CTAAAACGTGATGTTAGCGGGAATTTACTTTGTGTACTAATCCATAAATTCGATC-GATT
F.unbracteata    -TAATACGTAATGTTAGCGGGCATTTACTTTGTGTGCTAATCCATAAATTCGAACCGATT
F.pallidifl      -TAAAACGTGATGTTAGCGGGAATTTACTTTGTGTACTAATCCATAAATTCGATC-GATT
F.hubeinesis     -TAATACGTAATGTTAGCGGGCATTTACTTTGTGTGCTAATCCATAAATTCGACC-GATT
F.cir.var.pur    -TAATACGTAATGTTAGCGGGCATTTACTTTGTGTGCTAATCCATAAATTCGACC-GATT
F.puqiensis      -TAATACGTAATGTTAGCGGGAATTTACTGTGTGTACTAATCCATAAATTCGATC-GATT
F.delavayi       -TAATACGTAATGTTAGCGGGCATTTACTTTGTGTGCTAATCCATAAATTCGACC-GATT
F.thunbergii     -TAATACGTAATGTTAGCGGGAATTTACATTGTGTACTAATCCATGAATTCGATC-GATT
F.taibainesis    -TAATACGTAATGTTAGCGGGCATTTACTTTGTGTGCTAATCCATAAATTCGACC-GATT
F.anhuiensis     -TAATACGTAATGTTAGCGGGAATTTACTGTGTGTACTAATCCACAAATTCGAT-CGATT
F.ussunensis     -TAATACGTAATGTTAGCGGGCATTTACTTTGTGTGCTAATCCATAAATTCGAC-CGATT
F.tianmuensis    -TAATACGTAATGTTAGCGGGAATTTACTTTGTGTACTAATCCATAAATTCGAT-CGATT
F.prezwalskii    -TAAAACGTGATGTTAGCGGGAATTTACTTTGTGTACTAATCCATAAATTCGAT-CGATT
F.cir            -TAATACGTAATGTTAGCGGGCATTTACTTTGTGTGCTAATCCATAAATTCGACACGTTT
F.cirrhosa       -TAATACGTAATGTTAGCGGGCATTTACTTTGTGTGCTAATCCATAAATTCGACC-GATT
                  *** **** ************ ******  ***** ********  *******  * **

F.cir.var.vir    AATGCTAATATTTTAATAATTGGCTCTCGCTTTCCGTTTAGTA-GGATTAACTCCTAGTT
F.tortifoliae    AATGCTAATACTTTAATAATTGGCACTCGCTTTCCGTGTAATAAGGATTAACTCCTAATT
F.unbracteata    AATGCTAATATTTTAATAATTGGCACTCGCTTTCCTTTTAGTA-GGATTAACTCCTAGTT
F.pallidifl      AATGCTAATACTTTAATAATTGGCACTCGCTTTCCGTGTAATAAGGATTAACTCCTAATT
F.hubeinesis     AATGCTAATATTTTAATAATTGGCTCTCGCTTTCCGTTTAGTA-GGACTAACTCCTAGTT
F.cir.var.pur    AATGCTAATATTTTAATAATTGGCTCTCGCTTTCCGTTTAGTA-GGATTAACTCCTAGTT
F.puqiensis      AATGCTAATACTTTAATAATTGGCTCTCGCTTTCCGTGTAATAAGGATTAACTCCTAATT
F.delavayi       AATGCTAATATTTTAATAATTGGCTCTCGCTTTCCGTTTAGTA-GGACTAACTCCTAGTT
F.thunbergii     AATGCTAATACTTTAATAATTGGCTCTCGCTTTCCGTGTAATAAGGATTAACTCCTAATT
F.taibainesis    AATGCTAATATTTTAATAATTGGCTCTCGCTTTCCGTTTAGTA-GGACTAACTCCTAGTT
F.anhuiensis     AATGCAAATACTTCAATAATTGGCTCTCGCTTTCCGTGTAATA-GGATTAACTCCTAATT
F.ussunensis     AATGCTAATATTTTAATAATTGGCTCTCGCTTTCCGTTTAGTA-GGACTAACTCCTAGTT
F.tianmuensis    AATGCAAATACTTTAATAACTGCGTCTCGCTTTCCGTGTAATAAGGATTAACTCCTAATT
F.prezwalskii    AATGCTAATACTTTAATAATTGGCACTCGCTTTCCGTGTAATAAGGATTAACTCCTAATT
F.cir            AATGCTAATATTTTAATAATTGGCTCTCGCTTTCCGTTTAGTA-GGATTAACTCCTAGTT
F.cirrhosa       AATGCTAATATTTTAATAATTGGCTCTCGCTTTCCGTTTAGTA-GGATCAACTCCTAGTT
                 ***** **** ** ***** **  ********* ** ** *** *******  **
```

Figure 5E

```
F.cir.var.vir    TTGAAGCCCGTGGAAGAGGAATAAGAGGAAGGGGAAGGAAACAT-ATGACGGGTGCGATC
F.tortifoliae    TTGAATCCCGTGGAAGTTGAATAAGAGGAAGGGGAAGGAATCAT-ATGACGGGTGCGATC
F.unbracteata    TTGAAGCCCGTGGAAGAGGAATAAGAGGAAGGGGAAGGAAACAGTATGACGGGTGCGATC
F.pallidifl      TTGAATCCCGTGGAAGTTGAATAAGAGGAAGGGGAAGGAATCAC-ATGACGGGTGCGATC
F.hubeinesis     TTGAATCCCGTGGAAGAGGAATAAGAGGAAGGGGAAGGAAACAT-ATGACGGGTGCGATC
F.cir.var.pur    TTGAAGCCCGTGGAAGAGGAATAAGAGGAAGGGGAAGGAAACAT-ATGACGGGTGCGATC
F.puqiensis      TTGAATCCCGTGGAAGAGGAATAAGTGGAAGGGGAAGGAAACAT-ATGACGGGTGCGATC
F.delavayi       TTGAATCCCGTGGAAGAGGAATAAGAGGAAGGGGAAGGAAACAT-ATGACGGGTGCGATC
F.thunbergii     TTGAATCCCGTGGAAGAGGAATAAGTGGAAGGGGAAGGAAACAT-ATGACGGGTGCGATC
F.taibainesis    TTGAATCCCGTGGAAGAGGAATAAGAGGAAGGGGAAGGAAACAT-ATGACGGGTGCGATC
F.anhuiensis     TTGAATCCCGTGGAAGAGGAATAAGTGGAAGGGGAAGGAAACAT-ATGACGGGTGCGATC
F.ussunensis     TTGAATCCCGTGGAAGAGGAATAAGAGGAAGGGGAAGGAAACAT-ATGACGGGTGCGATC
F.tianmuensis    TTGAATCCCGTGGAAGAGGAATAAGTGGAAGGGGAAGGAAACAT-ATGACGGGTGCGATC
F.prezwalskii    TTGAATCACGTGGAAGTTGAATAAGAGGAAGGGGAAGGAATCAT-ATGACGGGTGCGATC
F.cir            TTGAAGCCCGTGGAAGAGGAATAAGAGGAAGGGGAAGGAAACAT-ATGACGGGTGCGATC
F.cirrhosa       TTGAAGCCCGTGGAAGAGGAATAAGAGGAAGGGGAAGGAAACAT-ATGACGGGTGCGATC
                 ****  * *******  ****** *************  **   **************

F.cir.var.vir    ATACCAGCACTAAGGATCC
F.tortifoliae    ATACCAGCACTAAGGATCC
F.unbracteata    ATACCAGCACTAAGGATCC
F.pallidifl      ATACCAGCACTAAGGATCC
F.hubeinesis     ATACCAGCACTAAGGATCC
F.cir.var.pur    ATACCAGCACTAAGGATCC
F.puqiensis      ATACCAGCACTAAGGATCC
F.delavayi       ATACCAGCACTAAGGATCC
F.thunbergii     ATACCAGCACTAAGGATCC
F.taibainesis    ATACCAGCACTAAGGATCC
F.anhuiensis     ATACCAGCACTAAGGATCC
F.ussunensis     ATACCAGCACTAAGGATCC
F.tianmuensis    ATACCAGCACTAAGGATCC
F.prezwalskii    ATACCAGCACTAAGGATCC
F.cir            ATACCAGCACTAAGGATCC
F.cirrhosa       ATACCAGCACTAAGGATCC
                 *******************
```

FRITILLARIA SPECIES IDENTIFICATION

This application is a continuation of application Ser. No. 09/352,061, filed Jul. 14, 1999, and which is now abandoned.

The present invention discloses methods for the identification of Fritillaria species.

Beimu, bulbs of the plant genus Fritillaria, is an important traditional Chinese herbal drug commonly used as an antitussive and expectorant (Li, P. et al., 1993, J. China Pharm. Univ. 24: 360–362). At least 25 species and varieties of Fritillaria are described as Beimu on commercial markets (Li, P. and Xu, G. J., 1993, J. Plant Res. Envir. 2: 12–17; Li, P. et al., 1990a, Chin. Trad. Herbal Drugs 21: 26–29; Li., P. et al., 1990b, J. China Pharm. Univ. 21: 19–25). However, these species and varieties differ extensively in terms of their medical efficacy, general abundance, price and toxicity (Liu, G. et al., 1996, Pharm. Res. 13: 10), and it is important for both producers, consumers and regulators to be able to identify the origin of a particular plant.

Current approaches to herbal identification depend on morphological, anatomical and chemical analyses, but these characteristics are often affected by environmental and/or developmental factors during plant development (Li, P. et al., 1994, J. Plant Res. Envir. 3: 60–63; Li, P. et al., 1991, Acta Bot. Yunnanica 13: 41–46). Many of the Fritillaria species have bulbs which are very difficult to differentiate by anatomical and morphological characteristics. Furthermore, chemotaxonomical studies can be hampered by the crude processing techniques often employed in the preparation of herbal medicines.

Work disclosed here shows for the first time that the 5S-ribosomal RNA (5S-rRNA) gene sequence contains spacer regions (introns) which are polymorphic for Fritillaria species. In all higher eukaryotes coding regions of the 5S-rRNA gene are separated from each other by simple spacers. The gene occurs as a tandem repeated unit (cistron) consisting of a ±120 bp coding region separated by a 300 bp spacer region (Dovorak, J. et al., 1989, Genome 32: 1003–1016). The spacer regions are valuable in different species. Experiments (below) show that informative DNA sequence differences exist in the sixteen Fritillaria species and varieties examined (SEQ ID NOs: 1–16, FIGS. 5A through 5E). 5S-rRNA DNA sequences have been used to rapidly differentiate between Fritillaria species using a variety of techniques which enable comparison between the DNA sequence.

Plant phylogenisation is known in the art (see for example GB 2310718, U.S. Pat. No. 5,849,492, U.S. Pat. No. 5,738,988, U.S Pat. No. 5,723,507) but it has not been previously suggested that it may be achieved by the method of the present invention.

Thus according to the present invention there is provided a method for determining the phylogeny of sample Fritillaria genetic material, comprising the steps of:
  i) characterising the spacer region of the 5S-rRNA gene of said sample genetic material;
  ii) comparing the characterised sample genetic material of step (i) with a characterised 5S-rRNA gene spacer region of control Fritillaria genetic material having a known phylogeny; and
  iii) correlating the results of comparison step (ii) to determine the phylogeny of the sample genetic material.

The method of the present invention may be used to determine the exact phylogeny of sample genetic material, or it may alternatively be used to provide negative results i.e. determine what the sample genetic material phylogeny is not. The method may also be used to determine the quantity of sample Fritillaria genetic material. Thus the method may be used to determine the presence and quantity of specific Fritillaria genetic material in a sample.

As well as being applicable to determining the phylogeny of sample Fritillaria genetic material (e.g. determine its species and variety), the method of the present invention may also be applied to other genetic material, particularly other plant genetic material. Thus as well as determining the species of genetic material, it may be used to determine the phylogeny of genetic material (e.g. determine its genus, family etc.). Naturally, in such a method to determine the phylogeny of non-Fritillaria genetic material, the control genetic material used would have to be non-Fritillaria.

The spacer region may be characterised by any desired technology, for example by sequencing, restriction fragment length polymorphisms (RFLP), polymerase chain reaction (PCR) (for example using discriminatory primers), 5S-rRNA gene spacer region length polymorphism and single strand conformational polymorphisms (SSCP). Discriminatory oligonucleotide primers may also be employed in PCR reactions according to the present invention. By using PCR technology, nanogram quantities of DNA are required to amplify and yield sufficient amount of template DNA for molecular genetic analysis.

Alternatively, characterisation may be achieved by studying the said (sample or control) hybridisation of a single strand of genetic material to a complementary strand of genetic material having known characteristics. This complementary strand of genetic material may include a known sequence or sequences or have a sequence or sequences which are specifically phylogeny-related, or it may simply be of a known phylogeny, i.e. the sequence need not be known. The complementary genetic material may be attached to a solid support in order to aid in the characterisation process. For example, hybridisation to a complementary strand at a specific position in an array of complementary strands may be assayed. The characterisation may be achieved using "gene chip" technology (Palecek, 1988, Bioelectrochemistry and Bioenergetics, 20: 179–199; Schena, M. et al., 1995, Science, 270: 467–470; Pease, A. C. et al., 1994, PNAS USA, 91: 5022–5026).

The DNA manipulation techniques employed in the present invention include those known to a person skilled in the art of characterising and differentiating between known and unknown genetic materials, for example: PCR (McPherson, M. J. et al., 1991, PCR: A practical approach, Oxford University Press, Oxford); DNA cloning and Southern hybridisation (Sambrook, J. et al., 1989, Molecular cloning: a laboratory manual, Cold Spring Harbour Laboratory, Cold Spring Harbour, N.Y.); restriction fragment length polymorphism (RFLP) (Davies, K. E., 1988, Genome analysis: a practical approach, IRL Press, Oxford); single strand conformational polymorphism (SSCP) (Orita, M. et al., 1989, PNAS USA 86 (8): 2766–2770); and sequencing (Sanger, F. et al., 1977, PNAS USA 74(12): 5463–5467).

The control genetic material used in any method according to the present invention may have the sequence of any one of the group comprising the introns of SEQ ID NOs: 1–16. These sequences include entire introns and it will be readily apparent to on skilled in the art that distinctive fragments (portions) of the introns may be used, i.e. fragments not shared by (common to) other known 5S-rRNA gene introns. Such distinctive fragments may be insufficiently complementary to a 5S-rRNA spacer region of a non-control organism to prevent specific detection of said nucleic acid molecule hybridized with said control 5S-rRNA nucleic acid under stringent hybridization conditions.

The sample genetic material may comprise genomic DNA. Genomic DNA may be isolated from Fritillaria species and varieties using standard techniques (see for example Gelvin, S. B. et al., 1993, Plant molecular biology manual, Kluwer Academic, Dordrecht).

Also provided according to the present invention is a nucleic acid probe for determining the phylogeny of sample Fritillaria genetic material comprising a nucleic acid selected from any one of the group of the introns of SEQ ID NOs: 1–16 or a distinctive fragment thereof. The nucleic acid probe may be free in solution for specifically detecting the presence or amount of a target organism or group of organisms containing ribosomal nucleic acid, in a sample which may include non-target organisms containing ribosomal nucleic acid.

Also provided according to the present invention is the use of a sequence selected from any one of the group consisting the introns of SEQ ID NOs: 1–16 or a distinctive fragment thereof in the manufacture of a kit for determining phylogeny of sample Fritillaria genetic material.

Also provided according to the present invention is a test kit for determining the phylogeny of sample Fritillaria genetic material characterised in that it comprises at least one sequence selected from the group consisting the introns of SEQ ID Nos: 1–16 or a distinctive fragment thereof.

Experiments (below) have shown that not only is there polymorphism in the 5S-rRNA gene spacer region at an intra-species level, but also at the intra-variety level. Thus the method of the present invention may determine the species or variety of sample genetic material obtained from the genus Fritillaria.

The invention will be further apparent from the following description and the accompanying Figures which show by way of example only tests for determining the phylogenetic origin of different Fritillaria species.

BRIEF DESCRIPTION OF THE FIGURES

FIGS. 3A and 3B show a DNA sequence alignment of the spacer region of 5S-rRNA genes from Fritillaria puqiensis (SEQ ID NO: 7) *F. anhuieusis* (SEQ ID NO: 11), *F. thunbergii* (SEQ ID NO: 9) and *F. cirrhosa* (SEQ ID NO: 6). The coding sequences are underlined. The positions of primer sequences S-1 (SEQ ID NO: 17) and AS-1 (SEQ ID NO: 18) used for amplification are double underlined. Identical sequences are indicated by an asterisk (*). Gaps (–) are introduced for the best alignment.

FIGS. 5A through 5E show a DNA sequence alignment of the spacer region of 5S-rRNA genes from *Fritillaria cirrhosa* var. vir (SEQ ID NO: 1), *F. tortifoliae* (SEQ ID NO: 2), *F. unbraeteata* (SEQ ID NO: 3), *F. pallidifl* (SEQ ID NO: 4), *F. hubeinesis* (SEQ ID NO: 5), *F. cirrhosa* var. pur (SEQ ID NO: 6), *F. puqiensis* (SEQ ID NO: 7), *F. delavayi* (SEQ ID NO: 8), *F. thunbergii* (SEQ ID NO: 9), *F. taibainesis* (SEQ ID NO: 10), *F. anhuiensis* (SEQ ID NO: 11), *F. ussunensis* (SEQ ID NO: 12) and *F. tianmuensis* (SEQ ID NO: 13), *F. prezwalskii* (SEQ ID NO: 14), *F. cir* (SEQ ID NO: 15), *F. cirrhosa* (SEQ ID NO: 16). The coding sequences are underlined. Identical sequences are indicated by an asterisk (*). Gaps (–) are introduced for optimal alignment.

EXPERIMENTAL

Figure 1:
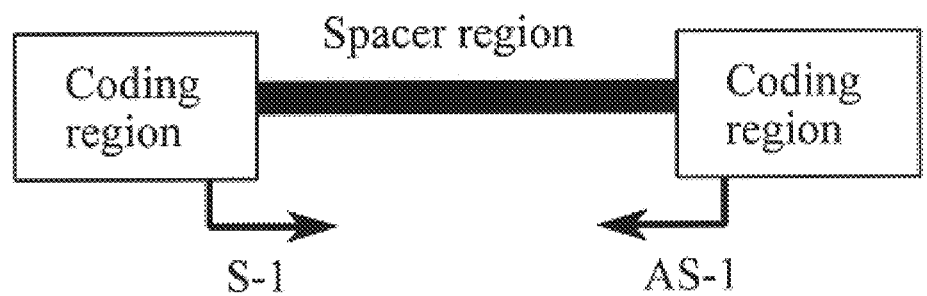
FIG. 1 shows the basic structure of the repeating units in 5S-rRNA gene cluster in higher plants. The coding region is ±120 bp in length, while the spacer region (intron) is ±600 bp in length. The positions of primers S-1 (SEQ ID NO: 17) and AS-1 (SEQ ID NO: 18) flanking the spacer region are shown.

The experiments described below detail the identification of unique 5S-rRNA spacer region sequences from several Fritillaria species and varieties. Total genomic DNA was extracted from fresh plant material, and 5S-rRNA spacer regions amplified by PCR with a pair of primers located within a conserved coding region. Cloned spacer regions were sequenced and aligned to reveal unique characteristics between 5S-rRNA spacer regions of the different Fritillaria species and varieties examined. Subsequent methods show rapid and accurate determination of the phylogenetic origin of Fritillaria test material.

Experiment 1

Material and Methods

Plant Material

All Fritillaria plant material was collected in the field in China. *F. cirrhosa* was obtained from Yunnan province, *F. thunbergii* from Ningbo, Zhejiang province, *F. anhuiensis* from Jinzai county, Anhui province, and *F. puqiensis* from Puqi, Hubei province. Plants were greenhouse-cultivated prior to DNA extraction, for which fresh leaves and bulbs were used. Sample of the tested species were stored dry for further identification. Normally, 4 to 5 different samples were tested in each Fritillaria species.

DNA Extraction

Plant genomic DNA was extracted according to Wu, T. et al. (1998) Chin. Trad. Herbal Drugs 29: 37–39, with the following minor modifications. The fresh leaves and bulbs were frozen with liquid nitrogen and ground into powder. Genomic DNA was extracted from the ground powder by using DNA extraction buffer consisting of 25 mM Tris-HCl, pH 8.0, 50 mM EDTA, 0.5% SDS, 10 µg/ml RNase, 0.2% 2-mercaptoethanol. The mixed solution was incubated for 15 min at 58° C., then centrifuged. The supernatant was extracted by equal volume of water saturated phenol: chloroform (1:1), mixed and then centrifuged. The aqueous phase was collected and added to 0.1 volume of 3M sodium acetate and 2 volumes of 100% ethanol. The resulting pellet was collected after centrifugation and dissolved in Tris EDTA buffer pH 8.0.

PCR Amplification

A 50 μl PCR reaction mix consisted of 5 μl 10×PCR reaction buffer, one μl each of 10 mM dNTPs stock, 2.5 μl forward and reverse primer (synthesized by GIBCO-BRL, Grand Island, N.Y.) and 1 unit of Taq polymerase (Boehringer Mannheim, Indianapolis, Ind.). Primers used for amplification of 5S-rRNA were S-1 forward primer (SEQ ID NO: 17) and AS-1 reverse primer (SEQ ID NO: 18). These primers flank the spacer domain of 5S-rRNA (Mizukami, H., 1995, Biol. Pharm. Bull. 18:1299–1301). Approximately 50 ng of genomic DNA was used as a template for the reaction. The reaction mix was overlaid with mineral oil and placed in a Robocycle Gradient 40 (Stratagene, La Jolla, Calif.). Cycling conditions consisted of an initial 5 min at 94° C. followed by 1 min denaturing at 94° C., 2 min annealing at 53° C. and 3 min elongation at 72° C. repeated for 30 cycles and with 10 min extension at 72° C. The PCR products were subjected to agarose gel electrophoresis and visualized by ethidium bromide staining under UV. DNAs were separated by 1% agarose gel, and then purified by agarose Gel DNA Extraction Kit (Boehringer Mannheim).

Subcloning and Sequencing

PCR products were subcloned into a TA cloning vector pTAg (R&D Systems, UK). The ligated products were transformed into E. Coli JM 109, and the colonies identified by colour selection were picked and grown in 3 ml of Luria-Bertani (LB) liquid medium overnight. The mini-preparation of plasmid DNAs from the transformed cultures was performed using alkaline lysis (Sambrook, J. et al, 1989, supra). DNA inserts were verified by restriction analysis. The plasmid DNAs from verified colonies were also isolated with the Wizard Minipreps DNA purification system (Promega, Madison, Wis.).

DNA sequencing (Sanger, F. et al., 1977, supra) was undertaken using [α-$^{35}$S] dATP and T7 Sequencing Kit (Pharmacia Biotech, Sweden). About 5 μg of purified double stranded plasmid DNA was denatured in 0.2 volumes of 2 M NaOH for 10 min. The mixture was neutralized by adding 3M sodium acetate, and the DNA precipitated in 2 volumes of ethanol at −80° C. for 30 min. The DNA was dissolved in a mixture of Sequenase reaction buffer and primer. The primers used were T7 promoter, S-1, AS-1 and SEQ3' primers. The annealing reaction was performed by heating the DNA mixture to 65° C. and then cooling to 37° C. In the labelling mixture, DTT, labelling mix A, [α-$^{35}$S] dATP and Sequenase were added to the annealed DNA, and labelled at 37° C. for 5 min. In the termination reaction, 4 μl of labelling reaction was transferred to each of the 4 termination mixtures containing ddG, ddA, ddT and ddC, respectively. Finally, the reaction was stopped by adding the T7 Sequencing Kit Stop Solution. The reaction mixtures were heated to 76° C. before loading onto a 6% (w/v) acrylamide/bis-acrylamide (Sigma, St. Louis, Mo.), 7M Urea gel in 1×TBE buffer. The gel was dried under vacuum at 80° C. for 2 h and exposed to a Kodak BioMax film for at least 12 h. Both strands of DNA were sequenced 3 to 4 times so as to obtain a consensus sequence. The DNA sequences were read and digitized by a MacroRead Digitizer (Pharmacia, Uppsala). DNASIS and MacVector softwares (Kodak, New Haven, Conn.) were used for analysis.

PCR-RFLP

PCR products of 5S-rRNA spacer region were digested with 10 units of EcoR I at 37° C. for 1 hr. The DNAs were fractionated by 1.2% agarose gel electrophoresis and visualized by ethidium bromide staining under UV.

Results and Discussion

Figure 2:
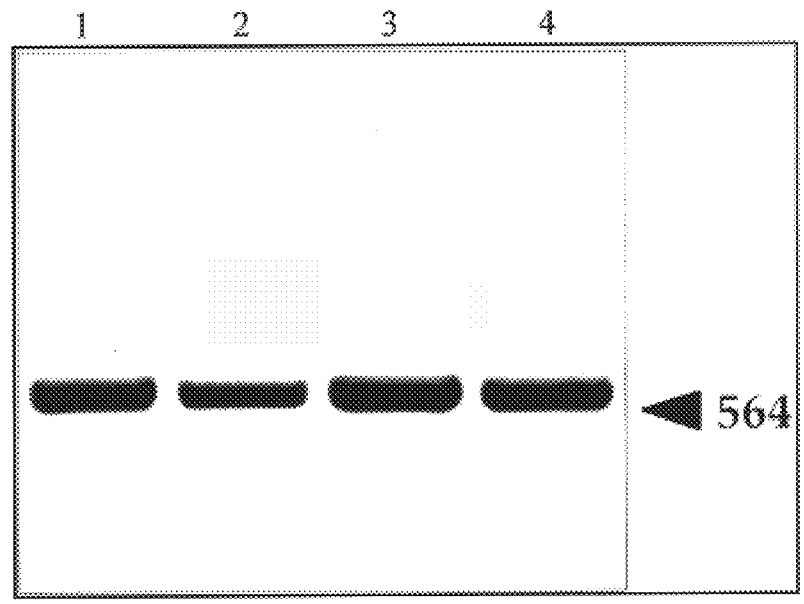
FIG. 2 shows PCR products generated by primers S-1 and AS-1 (SEQ ID NOs: 17 & 18, respectively) flanking the spacer region of the 5S-rRNA gene in Fritillaria. DNA templates were *F. puqiensis* (lane 1), *F. anhuiensis* (lane 2), *F. thunbergii* (lane 3) and *F. cirrhosa* (lane 4). PCR products were separated in a 1.2% agarose gel. Same size of PCR product was obtained from separately tested samples (n=4). An arrowhead indicates the position of a 564 bp DNA marker.

Primers flanking the spacer domain of 5S-rRNA were used in PCR analysis of genomic DNAs isolated from different Fritillaria species (FIG. 1). The PCR products of 4 tested species were sized at about 600 bp in the electrophoresis analysis (FIG. 2). Various tested samples gave the same size of PCR product. These PCR products were subcloned and sequenced. At least 3 individual clones of the same PCR product were sequenced to avoid any mutation introduced by Taq polymerase. The length of the F. cirrhosa amplification is 604 bp, F. thunbergii 589 bp, F. anhuiensis 595 bp, and F. puqiensis 595 bp (FIGS. 3A and 3B). Identical sequences were obtained when the amplification used DNAs isolated either from fresh leaf, or fresh bulb or dry crude herb from the same Fritillaria species as templates. The DNA sequence of the spacer region was unchanged regardless of the geographical origin of the Fritillaria species. The spacer domain among all Fritillaria species is highly conserved (~82%; FIGS. 3A and 3B). However, intra-species sequence variations were revealed. The sequences of F. cirrhosa at 22–35bp and 230–240bp are unique, while the sequence at 130–145bp is specific only to F. thunbergii, F. anhuiensis and F. puqiensis. The DNA sequence homology and number of transitions/transversions of different species of Fritillaria are shown in Table 1.

TABLE 1

DNA sequence homology and transition/transversion of the 5S-rRNA spacer region of four Fritillaria species

| | F. cirrhosa | F. thunbergii | F. piqiensis | F. anhuiensis |
|---|---|---|---|---|
| F. cirrhosa | — | 0.0480/ 0.0414[a] | 0.0464/ 0.0447[a] | 0.0513/ 0.0430[a] |
| F. thunbergii | 0.7881[b] | — | 0.034/ 0.0051[a] | 0.221/ 0.0102[a] |
| F. puqiensis | 0.8212[b] | 0.9745[b] | — | 0.0134/ 0.0101[a] |
| F. anhuiensis | 0.8278[b] | 0.9474[b] | 0.9748[b] | — | a - % Transition/% Transversion
b - Nucleotide sequence homology

The sequence of F. cirrhosa is 78.81% identical to that of F. thunbergii, 82.78% to that of F. anhuiensis, and 82.12% to that of F. puqiensis. The sequence of F. thunbergii is 94.74% identical to that of Fanhuiensis and 97.45% to that of F. puqiensis. The sequence of F. anhuiensis is 97.48% identical to that of F. puqiensis. There is more transition than transversion among different species. The highest homology among all species exists between F. thunbergii and F. puqiensis as well as between F. anhuiensis and F. puqiensis. Each Fritallaria species was found to have a unique sequence in the 5S-rRNA spacer region, so that they could be easily distinguished at the DNA level.

Figure 4A:
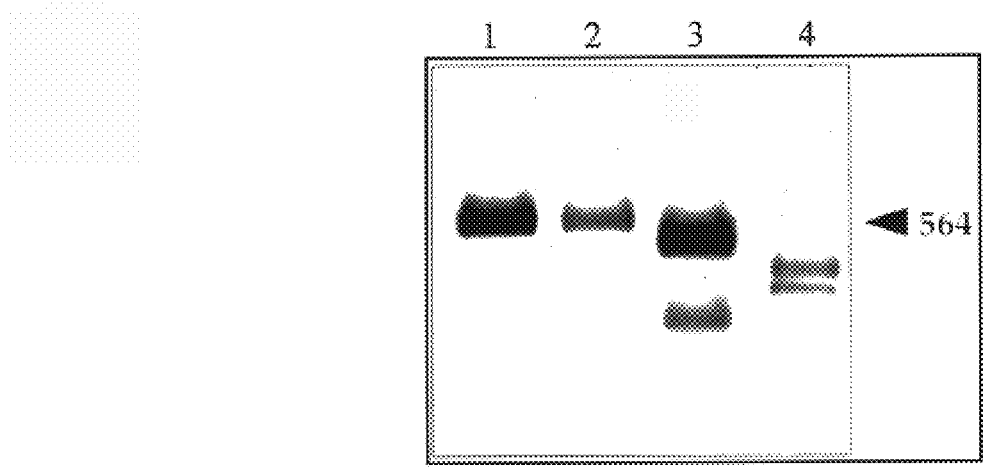
FIG. 4 shows the result of PCT-RFLP using the restriction endonuclease EcoRI. (A) EcoRI-digested PCR products of 5S-rRNA gene spacer regions of *Fritillaria puqiensis* (lane 1), *F. anhuiensis* (lane 2), *F. thunbergii* (lane 3) and *F. cirrhosa* (lane 4) were fractionated through a 1.2% agarose gel and visualised by ethidium bromide staining under UV. Similar results were obtained in four separate experiments. (B) EcoRI-digested PCR products of 5S-rRNA gene spacer regions of: *Fritillaria thunbergii* genomic DNA extracted from plants collected in Nanjing (lane 1), Ningbo (lane 2) and Nantong (lane 3) provinces in China; and *F. cirrhosa* genomic DNA extracted from dry bulb (lane 4), fresh leaf (lane 5) and crude drug (lane 6) material, treated as in (A)

From the identified sequences, an EcoRI site could be found in F. cirrhosa at 220–225 bp, while that of F. thunbergii is located at 466–471 bp (FIG. 4). In order to simplify the identification method, PCR products from F. cirrhosa, F. puqiensis, F. anhuiensis, or F. thunbergii DNA were digested with EcoR I. As expected, PCR products from F. cirrhosa and F. thunbergii could be digested by EcoR I, while F. anhuiensis and F. puqiensis were insensitive to the digestion. Two fragments of 384 bp and 314 bp were created from digested F. cirrhosa DNA, while fragments of 460 bp and 123 bp were revealed from the digested F. thunbergii DNA (FIG. 4A). This EcoRI site could be used for rapid and precise identification of F. cirrhosa from F. thunbergii.

Figure 4B:
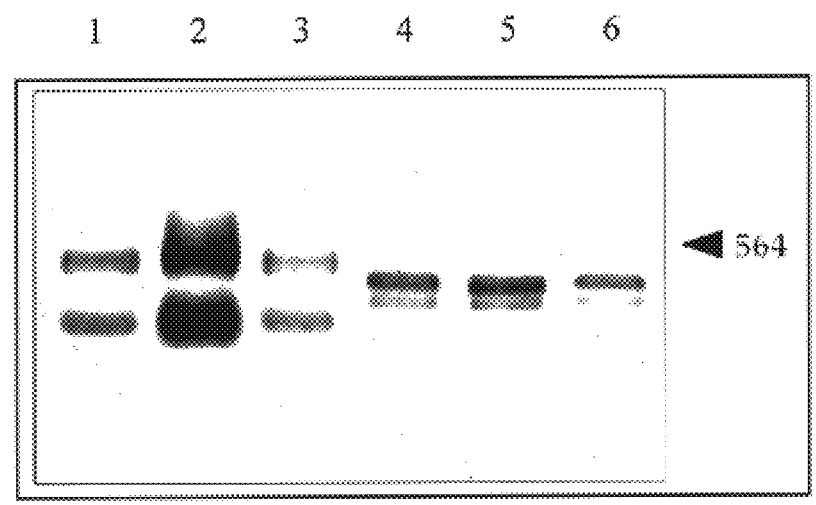

Regardless of the geographical origin or the source of DNA, the restriction profile of the spacer domain of Fritillaria remains unchanged (FIG. 4B).

Beimu falls into two categories in Chinese medicine: Chuan Beimu such as *F. cirrhosa* and Zhe Beimu such as *F. thunbergii*. They have different efficacy. The market price of Chuan Beimu is higher than that of Zhe Beimu, and Zhe Beimu is much more toxic than Chuan Beimu. At present, many young bulbs of Zhe Beimu are selling under the name of Chuan Beimu in China. However, it is difficult to identify them through traditional methods because the young bulbs of Zhe Beimu are similar to that of Chuan Beimu by appearance, microscopic characteristics and chemical constituents. Here, we developed a rapid and precise method of identification based on distinct sequences of Fritillaria. A unique EcoR I site on their 5S-rRNA spacer region could easily discriminate between *F. cirrhosa* and *F. thunbergii*. The discrimination could also be used to identify crude dry herbs.

Experiment 2

Using methods as discussed in Experiment 1 (supra), 5S-rRNA gene spacer regions were amplified using primers S-1 (SEQ ID NO: 17) and AS-1 (SEQ ID NO: 18) from sixteen Fritillaria species and varieties. DNA sequence alignment of these clones (SEQ ID NOS: 1–16) is shown in FIGS. 5A through 5E. These results extend those described in Experiment 1 (supra) by showing that each of the Fritillaria species and varieties compared have unique 5S-rRNA spacer region sequences.

What is claimed is:

1. A method for determining the species of a sample of Fritillaria genetic material comprising the steps of:
   i) comparing the 5s-rRNA gene spacer region of a sample of Fritillaria genetic material with at least one control 5s-rRNA gene spacer region of a known species of Fritillaria genetic material; and,
   ii) correlating the results of the comparison step (i) to determine the species of said sample of genetic material.

2. A method according to claim 1, wherein said comparing comprises sequencing.

3. A method according to claim 1, wherein said comparing comprises determining restriction fragment length polymorphisms.

4. A method according to claim 1, wherein said comparing comprises PCR.

5. A method according to claim 1, wherein said comparing comprises determining the length of the 5s-rRNA gene spacer region.

6. A method according to claim 1, wherein said comparing comprises detecting hybridization of a single strand of a polynucleotide to a complementary strand of the 5s-rRNA gene spacer region.

7. A method according to claim 6, said complementary strand being attached to a solid support.

8. A method according to claim 1, wherein said comparing comprises determining single strand conformational polymorphisms of said Fritillaria genetic material.

9. A method according to claim 1, said control region having the sequence of any one of the group consisting of SEQ ID NOs: 1–16 or a subsequence fragment thereof that specifically detects one of SEQ ID NOs: 1–16.

10. A method according to claim 1, wherein said sample genetic material comprises genomic DNA.

11. A nucleic acid probe for determining the species of sample Fritillaria genetic material consisting of a nucleic acid selected from a group consisting of SEQ ID NOs: 1–16 and fragments thereof that specifically detect one of SEQ ID NOs: 1–16.

12. A test kit for determining the species or variety of sample Fritillaria genetic material comprising at least one nucleic acid consisting of a sequence selected from the group consisting of SEQ ID NOs: 1–16 and fragments thereof that specifically defect one of SEQ ID NOs: 1–16.

13. A composition comprising a combination of nucleic acid probes of claim 11.

* * * * *

SEQUENCE LISTING

```
<160> NUMBER OF SEQ ID NOS:  18

<210> SEQ ID NO 1
<211> LENGTH: 684
<212> TYPE: DNA
<213> ORGANISM: Fritillaria cirrhosa var. vir
<220> FEATURE:
<221> NAME/KEY: intron
<222> LOCATION: (57)..(655)

<400> SEQUENCE: 1
ggatccgtgc ttgggcgaga gtagtactag gatgggtgac ctcctgggaa gtcctcgtgt      60
tgcaccccca accccctctt ttgtcgcatc attttgtcgc atcatgagaa atgcgcacgt     120
cctccttttg tgcgcctcgc cctaaatagg cgggcgaggt aacatcgtgt cggcctttca     180
ttttacgggt tttggcgggc ccgctttcga tacgggggc gagctggcta ttttctcgat     240
ggtttgataa gaataagtca aaatatgagt ttgtgaattc taataattgg ttaattagct     300
ttcaccttat gctcggtgag atagatcgta atttcggttt ataaatatta atattttgtt     360
aattattttt ttttacttta agataaataa gattaattcc taagtccggt ttaataacgg     420
taatatatcg caaattaact tttactccgt gtctaatgag aaaaggtaat aatatatgtt     480
tattgatact aatacgtaat gttagcgggc atttactttg tgtgctaatc cataaattcg     540
accgattaat gctaatattt taataattgg ctctcgcttt ccgtttagta ggattaactc     600
ctagttttga agcccgtgga agaggaataa gaggaagggg aaggaaacat atgacgggtg     660
cgatcatacc agcactaagg atcc                                           684

<210> SEQ ID NO 2
<211> LENGTH: 679
<212> TYPE: DNA
<213> ORGANISM: Fritillaria tortifoliae
<220> FEATURE:
<221> NAME/KEY: intron
<222> LOCATION: (57)..(650)

<400> SEQUENCE: 2
ggatccgtgc ttgggcgaga gtagtactag gatgggtgac ctcctgggaa gtcctcgtgt      60
tacaccccct cccccctttt tgtcgcatcc tgagaaatac gcacgtcctc cttttgcgtt     120
cctcgcccta aataggcggg cgagctaaca ttttgtcgcc ctttcatttt gcgggttttg     180
gcggcacaaa acggggcgg gcctcttttc gataacgggg gggcgaagtg gctattttcc     240
cgatggtttg atgagaataa gtcaaaattt gagtttctga atactaatta actttcgctt     300
```

```
tatgcttggt gagattagat cataatttcg gtttgttaat atcgatatta ggtcaattaa      360
cttttttact ataagataaa taagattaat tccaaagttc ggtttattaa tggtaatgta      420
tcgcaaatta acttttactc cgtgtttaat gagaataagt cgtaatattc gtttattgat      480
acctaaaacg tgatgttagc gggaatttac tttgtgtact aatccataaa ttcgatcgat      540
taatgctaat actttaataa ttggcactcg ctttccgtgt aataaggatt aactcctaat      600
tttgaatccc gtggaagttg aataagagga aggggaagga atcatatgac gggtgcgatc      660
ataccagcac taaggatcc                                                   679

<210> SEQ ID NO 3
<211> LENGTH: 674
<212> TYPE: DNA
<213> ORGANISM: Fritillaria unbracteata
<220> FEATURE:
<221> NAME/KEY: intron
<222> LOCATION: (57)..(645)

<400> SEQUENCE: 3
ggatccgtgc ttgggcgaga gtagtactag gatgggtgac ctcctgggaa gtcctcgcgt       60
tgcaccccca accccctctt ttgtcgcatc atgagaaatg cgcacgtcct cctttttgtgc     120 gcctcgccta aataggcggg cgaggtaaca tcgtgtcggc ctttcattt acgggttttg      180 gcgggcccgc ctttcgatac gggggcgag ctggctattt tctcgatggt ttgataagaa      240
taagtcaaaa tatgagtttg tgaattctaa taattggtta attagctttc accttatgct     300
cggtgagata agatcgtaat ttcggtttat aaatattaat atttttgttaa ttattttttt    360 ttactttaag ataaataaga ttaattccta agtccggttt aataacggta atatatcgca     420
aattaacttt tactccgtgt ctaatgagaa aaggtaataa tatatgttaa ttgatactaa     480
tacgtaatgt tagcgggcat ttactttgtg tgctaatcca taaattcgaa ccgattaatg     540
ctaatatttt aataattggc actcgctttc cttttagtag gattaactcc tagttttgaa      600
gcccgtggaa gaggaataag aggaagggga aggaaacagt atgacgggtg cgatcatacc      660
agcactaagg atcc                                                        674

<210> SEQ ID NO 4
<211> LENGTH: 683
<212> TYPE: DNA
<213> ORGANISM: Fritillaria pallidifl
<220> FEATURE:
<221> NAME/KEY: intron
<222> LOCATION: (57)..(654)

<400> SEQUENCE: 4
ggatccgtgc ttgggcgaga gtagtactag gatgggtgac ctcctgggaa gtcctcgttg       60
ttacaccccc tccccctttt tgtcgcatc ctgagaaata cgcacgtcct ccttttgcgt      120
tcctcgccct aaataggcgg gcgagctaac attttgtcgc cctttctttt gcgggttttg      180
gccggcacaa acgggggcc gggcctcttt tgataacggg gggctcggga agtggctatt      240
ttcccgatgg tttgatgaga ataagtcaaa atttgagttt gtaatactaa ttaactttct     300
cgtttatcgt tggtgagat tagatcataa tttcggtttg ttaatcatga tattaggcta     360
attaactttt ttactataag ataaataaga ttaattccaa agttcggttt attaatggta     420
atgtatcgca aattaacttt tactccgtgt taatgagaa taagtcgtaa tattcgttta      480
ttgatactaa aacgtgatgt tagcgggaat ttactttgtg tactaatcca taaattcgat     540
```

-continued

```
cgattaatgc taatacttta ataattggca ctcgctttcc gtgtaataag gattaactcc    600
taattttgaa tcccgtggaa gttgaataag aggaagggga aggaatcaca tgacgggtgc    660
gatcatacca gcactaagga tcc                                            683
```

```
<210> SEQ ID NO 5
<211> LENGTH: 697
<212> TYPE: DNA
<213> ORGANISM: Fritillaria hubeinesis
<220> FEATURE:
<221> NAME/KEY: intron
<222> LOCATION: (57)..(668)

<400> SEQUENCE: 5
ggatccgtgc ttgggcgaga gtagtactag gatgggtgac ctcctgggaa gtcctcgtgt     60
tgcaccccct accccctctt ttgtcgcatc attgtgtcgc atcatcttgt cgcatcatga    120
gaaatgcgca cgtcctcctt ttgtcgcct cgccctaaat aggcgggcga ggtaacatcg    180
tgtcggcctt tcattttacg ggttttggcg ggcccgcttt cgatacgggg ggcgagctgg    240
ctattttctc gatggtttga taagaataag tcaaaatata agtttgtgaa ttctaataat    300
tggttaatta gccttcacct tatgctcggt gagataagat cgtaatttcg gttcataaat    360
attaatattt tgttaattat ttttttttact ttaagataaa taagattaat tcctaagtcc    420
ggtttaataa cggtaatata tcgcaaatta acttttactc tgtgtctaat gagaaaaggt    480
aataatatat gcttattgat actaaatcgt aatgttagcg ggcatttact ttgtgtgcta    540
atccataaat tcgaccgatt aatgctaata ttttaataat tggctctcgc tttccgttta    600
gtaggactaa ctcctagttt tgaatcccgt ggaagaggaa taagaggaag gggaaggaaa    660
catatgacgg gtgcgatcat accagcacta aggatcc                             697
```

```
<210> SEQ ID NO 6
<211> LENGTH: 684
<212> TYPE: DNA
<213> ORGANISM: Fritillaria cirrhosa var. pur
<220> FEATURE:
<221> NAME/KEY: intron
<222> LOCATION: (57)..(655)

<400> SEQUENCE: 6
ggatccgtgc ttgggcgaga gtagtactag gatgggtgac ctcctgggaa gtcctcgtgt     60
tgcaccccca accccctctt ttgtcgcatc attttgtcgc atcatgagaa atgcgcacgt    120
ccaccttttg tgcgcctcgc cctaaatagg cgggcgaggt aacatcgtgt cggcctttca    180
ttttacgggt tttggcgggc ccgctttcga tacgggggc gagctggcta ttttctcgat    240
ggtttgataa gaataagtca aaatatgagt tgtgaattc taataattgg ttaattagct    300
ttcaccttat gctcggtgag atagatcgta atttcggttt ataaatatta atattttgtt    360 aattattttta ctttacttta agataaataa gattaattcc taagtccggt ttaataacgg    420
taatatatcg caaattaact tttactccgc gtctaatgag aaaagtaat aatatatgtt    480 tattgatact aatacgtaat gttagcgggc atttactttg tgtgctaatc cataaattcg    540
accgattaat gctaatattt taataattgg ctctcgcttt ccgtttagta ggattaactc    600
ctagttttga agcccgtgga agaggaataa gaggaagggg aaggaaacat atgacgggtg    660
cgatcatacc agcactaagg atcc                                            684
```

```
<210> SEQ ID NO 7
<211> LENGTH: 679
```

```
<212> TYPE: DNA
<213> ORGANISM: Fritillaria puqiensis
<220> FEATURE:
<221> NAME/KEY: intron
<222> LOCATION: (57)..(650)

<400> SEQUENCE: 7
ggatccgtgc ttgggcgaga gtagtactag gatgggtgac ctcctgggaa gtcctcgttg      60
ttgcaccccc tccccctttt ttgtcgcatc ctgagaaata cgcacgtcct ccttttgcgc     120
gcctcgccct aaataggcgg gcgagctaac atttgtcggc cttttcatttt gcgggttttg    180 gcggcacaaa acgggggcgg gcccgctttt cgataacggg ggggcgaagt ggctattttc     240
ccgatggttt gatgagaata agtcaaaatt tgagtttgtg aatactaatt aactttcgct     300
ttatgcttgg tgagattaga tcataatttc ggtttattaa tattgatatt ttgtcaatta    360
acttttttac tatgagataa ataggattaa ttccaaagtt cggtttatta atggtaatat     420
atcgcaaatt aacttttact gcgtgtttag tgagaataag tcgtaatatt cgtttattga    480
tactaatacg taatgttagc gggaatttac tgtgtgtact aatccataaa ttcgatcgat     540
taatgctaat actttaataa ttggctctcg ctttccgtgt aataaggatt aactcctaat     600
tttgaatccc gtggaagagg aataagtgga aggggaagga aacatatgac gggtgcgatc     660
ataccagcac taaggatcc                                                  679

<210> SEQ ID NO 8
<211> LENGTH: 697
<212> TYPE: DNA
<213> ORGANISM: Fritillaria delavayi
<220> FEATURE:
<221> NAME/KEY: intron
<222> LOCATION: (57)..(668)

<400> SEQUENCE: 8
ggatccgtgc ttgggcgaga gtagtactag gatgggtgac ctcctgggaa gtcctcgtgt     60 tgcacccccct accccctctt ttgtcgcatc attgtgtcgc atcatcttgt cgcatcatga    120
gaaatgcgca cgtcctcctt ttgtgcgcct cgccctaaat aggcgggcga ggtaacatcg     180
tgtcggcctt tcattttacg ggttttggcg ggcccgcttt cgatacgggg ggcgagctgg     240
ctattttctc gatggtttga taagaataag tcaaaatata agtttgtgaa ttctaataat     300
tggttaatta gccttcacct tatgctcggt gagataagat cgtaatttcg gttcataaat     360 attaatatttt tgttaattat ttttttact ttaagataaa taagattaat tcctaagtcc     420
ggtttaataa cggtaatata tcgcaaatta acttttactc tgtgtctaat gagaaaggt     480 aataatatat gcttattgat actaatacgt aatgttagcg ggcatttact ttgtgtgcta     540
atccataaat tcgaccgatt aatgctaata ttttaataat tggctctcgc tttccgttta     600
gtaggactaa ctcctagttt tgaatcccgt ggaagaggaa taagaggaag gggaaggaaa     660
catatgacgg gtgcgatcat accagcacta aggatcc                              697

<210> SEQ ID NO 9
<211> LENGTH: 673
<212> TYPE: DNA
<213> ORGANISM: Fritillaria thunbergii
<220> FEATURE:
<221> NAME/KEY: intron
<222> LOCATION: (57)..(644)

<400> SEQUENCE: 9
ggatccgtgc ttgggcgaga gtagtactag gatgggtgac ctcctgggaa gtcctcgttg     60
```

-continued

```
ttgcacccc  tccccctttt  tgtcgcatc   ctgagaaata  cgcacgtcct  ccttttgcgc    120
gcctcgccct  aaataggcgg  gcgagctaat  cggcctttca  ttttgcgggt  tttggcggca    180
caaaacgggg  gcgggcccgc  ttttcgataa  cgggggggcg  aagtggctat  ttcccgatg     240 gtttgatgag  aataagtcaa  aatttgagtt  tgtgaatact  aattaacttt  cgctttatgc    300
ttggtgagat  tagatcataa  tttcggtgta  ttaatattga  tattttgtca  attaactttt    360
ttactatgag  ataaatagga  ttaattccaa  agttcggttt  attaatggta  atatatcgca    420
aattaacttt  tactgcgtgt  ttagtgagaa  taagtcgtaa  tattcgttta  ttgatactaa    480
tacgtaatgt  tagcgggaat  ttacattgtg  tactaatcca  tgaattcgat  cgattaatgc    540 taatactta   ataattggct  ctcgctttcc  gtgtaataag  gattaactcc  taattttgaa    600
tcccgtggaa  gaggaataag  tggaagggga  aggaaacata  tgacgggtgc  gatcatacca    660
gcactaagga  tcc                                                          673

<210> SEQ ID NO 10
<211> LENGTH: 697
<212> TYPE: DNA
<213> ORGANISM: Fritillaria taibainesis
<220> FEATURE:
<221> NAME/KEY: intron
<222> LOCATION: (57)..(668)

<400> SEQUENCE: 10
ggatccgtgc  ttgggcgaga  gtagtactag  gatgggtgac  ctcctgggaa  gtcctcgtgt     60 tgcacccct   accccctctt  ttgtcgcatc  attgtgtcgc  atcatcttgt  cgcatcatga    120
gaaatgcgca  cgtcctcctt  ttgtgcgcct  cgccctaaat  aggcgggcga  ggtaacatcg    180
tgtcggcctt  tcattttacg  ggttttggcg  ggccgctttt  cgatacgggg  ggcgagctgg    240
ctattttctc  gatggtttga  taagaataag  tcaaaatata  agtttgtgaa  ttctaataat    300
tggttaatta  gccttcacct  tatgctcggt  gagataagat  cgtaatttcg  gttcataaat    360
attaatattt  tgttaattat  tttttttact  ttaagataaa  taagattaat  tcctaagtcc    420
ggtttaataa  cggtaatata  tcgcaaatta  acttttactc  tgtgtctaat  gagaaaaggt    480
aataatatat  gctattgat   actaaatcgt  aatgttagcg  gcatttact   ttgtgtgcta    540 atccataaat  tcgaccgatt  aatgctaata  ttttaataat  tggctctcgc  tttccgttta    600
gtaggactaa  ctcctagttt  tgaatcccgt  ggaagaggaa  taagaggaag  gggaaggaaa    660
catatgacgg  gtgcgatcat  accagcacta  aggatcc                              697

<210> SEQ ID NO 11
<211> LENGTH: 679
<212> TYPE: DNA
<213> ORGANISM: Fritillaria anhuiensis
<220> FEATURE:
<221> NAME/KEY: intron
<222> LOCATION: (57)..(650)

<400> SEQUENCE: 11
ggatccgtgc  ttgggcgaga  gtagtactag  gatgggtgac  ctcctgggaa  gtcctcgttg     60 ttgcacccc   tccccctttt  ttgtcgcatc  ctgagaaata  agcacgtcct  cctttcgcgc    120
gcctcgccct  aaataggcgg  gcgagctaac  atttgtcggc  ctttcatttt  gcgggttttg    180
gcggcacaaa  acggggcgg   gcccgctttt  cgataacggg  gggcgaagt   ggctattttc    240 tcgatggttt  gatgagaata  agtcaaaatt  tgagtttgcg  aatactaatt  aactttcgct    300
```

-continued

```
ctatgcttgg tgagattaga tcataatttc ggtttattaa tattgatatt ttgtcaatta      360 actttttac tataagataa ataagattaa ttccaaagtt cggcttatta acggtaatat       420
atcgtcaaat taacttttgc tccgtgttta atgagaataa gtcgtaatat tcgtttattg      480
atactaatac gtaatgttag cgggaattta ctgtgtgtac taatccacaa attcgatcga      540
ttaatgcaaa tacttcaata attggctctc gctttccgtg taataggatt aactcctaat     600
tttgaatccc gtggaagagg aataagtgga aggggaagga acatatgac gggtgcgatc       660 ataccagcac taaggatcc                                                   679
```

<210> SEQ ID NO 12
<211> LENGTH: 697
<212> TYPE: DNA
<213> ORGANISM: Fritillaria ussunensis
<220> FEATURE:
<221> NAME/KEY: intron
<222> LOCATION: (57)..(668)

<400> SEQUENCE: 12

```
ggatccgtgc ttgggcgaga gtagtactag gatgggtgac ctcctgggaa gtcctcgtgt      60
tgcaccccct accccctctt tgtcgcatc attgtgtcgc atcatcttgt cgcatcatga      120
gaaatgcgca cgtcctcctt tgtgcgcct cgccctaaat aggcgggcga ggtaacatcg      180
tgtcggcctt tcattttacg ggttttggcg ggcccgcttt cgatacgggg ggcgagctgg     240
ctattttctc gatggtttga taagaataag tcaaaatata agtttgtgaa ttctaataat    300
tggttaatta gccttcacct tatgctcggt gagataagat cgtaatttcg gttcataaat    360
attaatattt tgttaattat ttttttttact ttaagataaa taagattaat tcctaagtcc   420
ggtttaataa cggtaatata tcgcaaatta acttttactc tgtgtctaat gagaaaaggt    480
aataatatat gcttattgat actaatacgt aatgttagcg ggcatttact ttgtgtgcta    540
atccataaat tcgaccgatt aatgctaata ttttaataat tggctctcgc tttccgttta    600
gtaggactaa ctcctagttt tgaatcccgt ggaagaggaa taagaggaag gggaaggaaa    660
catatgacgg gtgcgatcat accagcacta aggatcc                             697
```

<210> SEQ ID NO 13
<211> LENGTH: 678
<212> TYPE: DNA
<213> ORGANISM: Fritillaria tianmuensis
<220> FEATURE:
<221> NAME/KEY: intron
<222> LOCATION: (57)..(649)

<400> SEQUENCE: 13

```
ggatccgtgc ttgggcgaga gtagtactag gatgggtgac ctcctgggaa gtcctcgttg     60 ttgcacccc tccccctttt tgtcgcatc ctgagaaata cgcacgtcct ccttttgtgc       120
gcctcgccct aaataggcgg gcgagctaac attttgtcgg cctttcattt tgcgggtttt    180
ggcggcacaa aacgggggcg ggcccgcttt cgataacgg gggggcgaa gtggctatt       240 tcccgatggt tgatgagaa taagactttt tttgagtttg tgaatactaa ttaactttcg    300
ctttatgctt ggtgagatta gatcataatt cggtgattaa tattgatatt tgtccttaa    360 cttttttact ataagataaa taagattaat tccaaagttc ggtttattaa tggtaatata    420
tcgcaaatta acttttacag cgtgtttggt gagaataagt cgtaatattc gtttattgat    480
actaatacgt aatgttagcg ggaatttact ttgtgtacta atccataaat tcgatcgatt    540
aatgcaaata ctttaataac tgcgtctcgc tttccgtgta ataaggatta actcctaatt    600
```

```
ttgaatcccg tggaagagga ataagtggaa ggggaaggaa acatatgacg ggtgcgatca      660
taccagcact aaggatcc                                                    678

<210> SEQ ID NO 14
<211> LENGTH: 682
<212> TYPE: DNA
<213> ORGANISM: Fritillaria prezwalskii
<220> FEATURE:
<221> NAME/KEY: intron
<222> LOCATION: (57)..(653)

<400> SEQUENCE: 14
ggatccgtgc ttgggcgaga gtagtactag gatgggtgac ctcctgggaa gtcctcttgt       60
tacaccccct cccccttttt tgtgatcctg agaaatacgc acgttcctcc ttttgccttt      120
cctcgcccta aataggcggg cgagctaaca ttttgtcgcc ctttcatttt gcggttttg      180 gcggcacaaa acgggggcgg gccctctttt cgataacggg gggtgaagtg gctattttcc      240
gatggtttga tgagaataag ttcaaaattt gagtttctga atactaattt aactttcgct      300
ttatgcttgg tgagattaga tcataatttt cagtttgtta atatcgatat taggtcaatt      360 aacttttta ctataagata aataagatta attccaaagt tcggtttatt aaatggtaaa       420
tgtatcgcaa attaactttt actccgtgtt taatgagaat aagtcgtaat attcgtttat      480
tgatactaaa acgtgatgtt agcgggaatt tactttgtgt actaatccat aaattcgatc      540
gattaatgct aatactttaa taattggcac tcgctttccg tgtaataagg attaactcct      600
aattttgaat cacgtggaag ttgaataaga ggaagggggaa ggaatcatat gacgggtgcg      660
atcataccag cactaaggat cc                                               682

<210> SEQ ID NO 15
<211> LENGTH: 681
<212> TYPE: DNA
<213> ORGANISM: Fritillaria cir
<220> FEATURE:
<221> NAME/KEY: intron
<222> LOCATION: (57)..(652)

<400> SEQUENCE: 15
ggatccgtgc ttgggcgaga gtagtactag gatgggtgac ctcctgggaa gtcctcgtgt       60 tgcaccccc aacccctct ttgtcgcat cattttatcg catcatgaga aatgcgcacg        120
tcctcctttt gtgcgcctcg ccctaaatag gcgggcgagg taacatcgtg tcggccttttc     180 attttacggg ttttggcggg cccgctttcg atacgggga gagctggcta ttttctcgat      240
ggtttgatga gaataagtca aaatatgagt ttgtgaattc taataattgg ttaattagct     300
ttcaccttat gctcggtgag ataagatcgt aatttcggtt ataaatatta atatttgtta    360 attattttt actttaagat aaataagatt aattccaaag tccggtttaa taacggtaat    420
atatcgcaaa ttaacttta ctccgtgttt aatgagaaaa ggtaataata tatgtttat      480 gatactaata cgtaatgtta gcggcatttt actttgtgtg ctaatccata aattcgacac     540
gtttaatgct aatattttaa taattggctc tcgctttccg tttagtagga ttaactccta   600
gttttgaagc ccgtgaaga ggaataagag gaagggggaa gaaacatatg acgggtgcga    660
tcataccagc actaaggatc c                                               681

<210> SEQ ID NO 16
<211> LENGTH: 688
<212> TYPE: DNA
```

-continued

```
<213> ORGANISM: Fritillaria cirrhosa
<220> FEATURE:
<221> NAME/KEY: intron
<222> LOCATION: (57)..(659)

<400> SEQUENCE: 16
ggatccgtgc ttgggcgaga gtagtactag gatgggtgac ctcctgggaa gtcctcgtgt      60
tgcaccccca acccctctt ttgtcgcatc attttgtcgc atcatgagaa atgcgcacgt     120
cctccttttg tgcgcctcgc cctaaatagg cgggcgaggt aacatcgtgt cggcctttca     180
ttttacgggt tttggcgggc ccgactttcg atacgggggg cgagctggct attttctcga     240
tggtttgata agaataagtc aaaatatgag tttgtgaatt ctaataattg gttaattagc     300
tttcacctta tccgatcggt gagataagat cgtaatttcg gtttataaat attaatattt     360
tgttaattat tttttttact ttaagataaa taagattaat tcctaagtcc ggtttaataa     420
cggtaatata tcgcaaatta acttttactc tgtgtctaat gagaaaaagg taataatata     480
tgcttattga tactaatacg taatgttagc gggcatttac tttgtgtgct aatccataaa     540
ttcgaccgat taatgctaat attttaataa ttggctctcg ctttccgttt agtaggatca     600
actcctagtt ttgaagcccg tggaagagga ataagaggaa ggggaaggaa acatatgacg     660
ggtgcgatca taccagcact aaggatcc                                        688

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer  S-1

<400> SEQUENCE: 17
ggatccgtgc ttgggcgaga gtagta                                           26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer AS-1

<400> SEQUENCE: 18
acgctagtat ggtcgtgatt cctagg                                           26
```